United States Patent [19]
Dubrow

[11] Patent Number: 5,427,729
[45] Date of Patent: Jun. 27, 1995

[54] METHOD OF MAKING GEL PACKED COLUMNS SUITABLE FOR USE IN CHROMATOGRAPHY

[75] Inventor: Robert S. Dubrow, San Carlos, Calif.

[73] Assignee: The Perkin-Elmer Corporation, Foster City, Calif.

[21] Appl. No.: 416,588

[22] Filed: Oct. 3, 1989

[51] Int. Cl.⁶ ................ B29C 47/36; B29C 43/20
[52] U.S. Cl. ................ 264/232; 264/211.12; 264/211.18; 264/267
[58] Field of Search ........... 264/232, 267, 101, 211.12, 264/211.13, 211.18, 102; 141/1, 5, 27, 31; 210/656; 204/182.8

[56] References Cited

U.S. PATENT DOCUMENTS

| | | | |
|---|---|---|---|
| 3,523,863 | 8/1970 | Juhos | 204/182.8 |
| 3,527,712 | 9/1970 | Renn et al. | 204/182.8 |
| 3,640,809 | 2/1972 | Polson et al. | 204/182.8 |
| 3,796,657 | 3/1974 | Pretorius et al. | 210/656 |
| 3,875,044 | 4/1975 | Renn et al. | 204/182.8 |
| 4,189,370 | 2/1980 | Boschetti | 204/182.8 |
| 4,208,284 | 6/1980 | Pretorius et al. | 210/767 |
| 4,549,584 | 10/1985 | Morin et al. | . |
| 4,597,421 | 6/1986 | Wells | . |
| 4,675,300 | 6/1987 | Zare et al. | 436/172 |
| 4,865,706 | 9/1989 | Karger et al. | 204/182.8 |
| 4,891,119 | 1/1990 | Ogawa | . |
| 4,966,792 | 10/1990 | Terai et al. | . |

*Primary Examiner*—Jan H. Silbaugh
*Assistant Examiner*—A. Y. Ortiz
*Attorney, Agent, or Firm*—John A. Frazzini; Peter J. Dehlinger

[57] ABSTRACT

A method of filling a capillary with a substantially void-free gel by forming the gel outside of the capillary and then extruding the gel into the capillary. The initial gel can be formed as a rod of gel much larger in diameter than the capillary into which it is to be extruded. This rod of gel is rinsed to remove polymerization contaminants and then dried to form a dried gel preform. The gel can be resolvated with a compatible solvent and then extruded into one or more capillaries.

4 Claims, 4 Drawing Sheets

METHOD OF MAKING GEL PACKED COLUMNS SUITABLE FOR USE IN CHROMATOGRAPHY

In the figures, the first digit of a reference numeral will indicate the first figure in which is presented the element indicated by that reference numeral.

BACKGROUND OF THE INVENTION

This invention relates in general to gel chromatography and relates more particularly to methods of producing a gel-packed column for use in electrophoresis chromatography. A gel is a cross-linked polymer network swollen in a solvent medium.

The field of chromatography is discussed in A. Braithwaite and F. J. Smith, *Chromatographic Methods*, Chapman and Hall, Fourth Edition. A discussion of electrophoresis is presented in U.S. Pat. No. 4,675,300 entitled Laser-Excitation Fluorescence Detection Electrokinetic Separation issued to Richard N. Zare on Jun. 23, 1987. In chromatography, two components in a sample are separated by passing the sample through a medium in which one component travels at a faster rate than the other component. In general, this is achieved by utilizing a mobile phase and a stationary phase. The mobile phase can be a gas or a liquid and the stationary phase can be a solid or can be a liquid supported on a solid or on a gel. It is very common today to include one or more sensors along the chromatography column to detect the samples as they pass such sensors. For example, a spectrophotometer can be connected to the chromatograph to not only detect the passage of sample peaks, but also to measure the spectral absorption of each peak to identify the sample component or components in each peak.

In ion exchange chromatography, the samples have affinities for both the mobile phase and the stationary phase. A sample having a relatively greater affinity for the mobile phase than for the stationary phase will spend a greater fraction of its time in the chromatograph attached to the mobile phase and therefore will travel along the chromatograph at a greater speed than does another sample component having a smaller relative affinity for the mobile phase. Ion exchange chromatography therefore separates samples according to their relative affinity for these two phases. Various choices of mobile and stationary phases can be made to optimize the separation of the expected sample components.

Gel chromatography has been found to be particularly useful for separating biological molecules from organic mixtures (see, Braithwaite and Smith, sections 4.5, 4.8 and 4.9). Gels are produced by a polymerization process that produces porous structures, each consisting of a cross-linked polymer having a pore size that is regulated by controlling the amount of cross-linking. Gels typically contain on the order of 0.5–15 weight % cross-linked polymer and 55–99.5 weight % solvent. Such a three-dimensional lattice allows diffusion of molecules through the lattice at rates that are dependent on the relative sizes of the molecules to the pores in the lattice. Such separation by size and shape is important in biological chemistry because biological molecules exhibit a greater range of size and shape than of chemical affinity as is important in ion-exchange chromatography.

The most common geometries for the gels are gel slabs and gel columns. The passage of electric current in traditional systems with gel slabs and columns having diameters and thicknesses on the order of millimeters and greater, produces an undesired amount of Joule heating. Such heating can distort the gel structure, thereby interfering with the sample component separation process. To avoid the need for cooling systems to remove such heat, the trend has been away from traditional chromatography columns and toward the use of capillaries having diameters on the order of tens to hundreds of microns. The increased surface-to-volume ratio enhances heat removal and the smaller bore decreases the amount of sample required for a measurement, improves the measurement accuracy and increases the speed of measurement.

In gel ion-exchange chromatography and gel permeation chromatography, the gel is generally formed into beads that are on the order of 10's to 100's of microns in diameter with a pore size that is on the order of the size of the sample particles that are to be separated (typically on the order of a few to millions of Angstroms). These beads are poured into one end of the chromatograph column as a slurry of solvated beads and are prevented from exiting the other end of the column by a frit (i.e., a porous matt) attached to the other end of the column to restrain the beads. The bead size is selected to be as small as possible while still allowing an adequate flow rate of sample and eluent through the chromatograph. The amount of compaction of the mass of beads is kept low enough that the larger molecules have a free pathway to travel around the beads.

In gel permeation chromatography, only the sieve-like structure of the gel is utilized to separate the sample components so that separation is substantially independent of the chemical affinities of the sample components. In gel ion-exchange chromatography, both the sieve-like nature of a gel and the chemical affinity of electrolytes in the chromatograph are utilized to produce the sample separations.

In gel ion-exchange chromatography, the sample is carried along the chromatograph by an electrolyte having ions that have a chemical affinity for the gel. Sample ions on the gel are displaced by ions in the mobile phase of the same sign of charge as the displaced ions. The ion-exchange mechanism takes place in the thin film of solvent at the surface of the bead, including those portions of the surface adjacent to the pores of the bead. Ions comparable to or larger than the pore size are excluded from the interior of the resin so that only ions smaller than the pore size diffuse within the lattice flamework of a bead. Such small ions therefore experience the large surface area interior of a bead and therefore experience a large number of ion exchange interactions with the resin or gel, thereby travelling along the chromatograph at a slower rate than the ions that are larger than the pore size. These smaller atoms experience the full ion-exchange capacity of the resin or gel, which is defined to be the amount of charged groups per gram of dry resin or gel. Any compounds that are completely excluded from the gel will not be separated from each other and any compounds that completely penetrate the gel will not be separated from each other.

The ion exchange process is an equilibrium process in which the affinity between the exchange ion and the bead surface is a function of the chemistry of both the exchange ion and the bead. Ions with a large affinity for the bead travel along the chromatograph more slowly than ions with smaller affinity so that the rate of travel is dependent on such affinity as well as on the ratio between ion and pore sizes. Depending on the pH, the sample ions can attach to the beads strongly enough that they form a substantially stationary band within the chromatograph. An eluent with a pH sufficient to displace the bound sample ions is then used to wash the sample along the chromatograph. The bound ions will be eluted in descending order of their affinity for the beads. The available ion-exchange capacity is the actual capacity that results under experimental conditions and is dependent on the accessibility of functional groups, on eluent concentration, on ionic strength and pH, on the nature of the counter ions and on the strength of the ion exchanger and its degree of cross-linkage.

In FIG. 1 is illustrated an apparatus for electrophoretic separation chromatography. A first buffer solution 11 is contained in a container such as beaker 13 and a second buffer solution 12 is contained in a second container such as beaker 14. Each end of a capillary 15 is immersed in one of these two beakers and a voltage source 16 produces a voltage difference between these solutions on the order of 5–30 kV and a current through capillary 15 on the order of 1–25 $\mu$A. Capillary 15 has an inside diameter on the order of 2–500 $\mu$m and a length that is typically in the range from 20 cm to a meter. Although the typical range of capillary diameters is 2–500 $\mu$m, other diameters can also be used. In particular, the method described below is also useful for larger diameter capillaries. However, for such larger diameter capillaries, other methods of filling the capillaries are available.

In FIG. 2 is illustrated in greater detail a small section of capillary 15. The interior cavity 20 of capillary 15 is filled with a conductive liquid referred to as the "support electrolyte". Wall 21 of capillary 15 adsorbs ions 22 (which in this embodiment are negative, but for other choices of support electrolyte and wall 21 can be positive), thereby leaving an excess of positively charged ions 23 in the body 24 of the support electrolyte. Voltage source 16 produces an electric field $\vec{E}$ that drives positively charged fluid body 24 toward the cathode of voltage source 16. In addition, positively charged particles are driven toward the cathode and negatively charged particles, such as particle 25, are driven toward the anode of voltage source 16. Sample is loaded into capillary 15 by immersing the inlet end of the capillary into a vial containing the sample and briefly turning on the electric field to draw some of the sample into the capillary. The inlet end of the capillary is then reinserted into beaker 13 and the electric field is turned on to draw sample ions from beaker 13 through capillary 15.

Many biological molecules are amphoteric so that the pH of the support electrolyte can be selected to control the sign of charge on selected sample components. Because of this ability to control the charge of sample components, some sample component separation can be achieved by this control of the charge of the sample components. However, because biological molecules have a greater variation in size and shape than in charge, it is advantageous to fill interior cavity 20 of capillary 15 with a gel having a pore size selected to separate selected components of the sample as the primary separation mode. Unfortunately, for a variety of reasons, it is difficult to achieve a continuous gel within cavity 20.

In gel electrophoresis chromatography, the gel is typically produced inside the capillary by mixing the gel precursors (typically including reactive monomers or prepolymers, one or more crosslinking agents, polymerization catalyst, polymerization initiator and other additives that may be useful during the separation process such as surfactants and denaturizers), filling the capillary with this mixture and allowing the gel to cure within the capillary. Unfortunately, in addition to the gel, this process leaves in the gel residues that can interfere with the chromatographic separation of sample components and lead to premature breakdown of the gel. Because of the extreme length to diameter ratio of capillary 15, these residues are not easily removed from the gel by flow of eluent through the capillary. Indeed, in electrophoresis, there is almost no flow of eluent through the gel. The only species that exhibit significant motion are the ionic species.

Another problem is that the gel generally shrinks by a few percent volume when it cures so that the gel tends to pull away from the walls of the capillary. As a result of this, when the electric field is turned on to push sample ions through the capillary, the gel tends to be pushed along and out of the capillary due to ionic groups associated with the gel. To prevent this, it is common to treat the inside surface of the capillary wall and/or to add to the gel precursor a coupling agent, such as silane, to bond the gel to the capillary wall.

An additional problem is that voids sometimes occur in the gel. Such voids are more readily produced in gels that are bonded to the capillary or column wall because they are prevented from pulling away from the wall as they shrink during curing. These voids present obstacles to the ionic flow and can introduce inhomogeneities in the process that degrade resolution. If such a void extends entirely across the internal diameter of the capillary, there will be a complete break in the current path and electrophoresis will be stopped.

To overcome the problem of voids, in one gel formation process, the capillary is first filled with the gel precursor. Preferably, the gel precursor is at a reduced temperature that inhibits the chemical reaction that results in formation of the gel. The capillary is then either heated or exposed to radiation in a narrow zone to cure the gel precursor within that zone. This zone is then moved along the capillary to cure the gel along the entire length of the capillary. By use of this moving zone of curing, the still mobile gel precursor can flow toward the cured zone to compensate for the shrinkage that occurs during curing. Unfortunately, this moving zone process is a slow process that is difficult to control and that significantly increases the time required to produce a gel within the capillary.

SUMMARY OF THE INVENTION

A method is presented of completely filling a capillary with gel. This process can be used to fill only part of the length of the capillary, but will generally be used to fill substantially the entire length of the capillary. Such gel-filled capillaries are particularly useful for electrophoretic chromatography, but are also useful for other purposes including gel permeation chromatography and gel ion-exchange chromatography.

In accordance with the illustrated preferred embodiment, a gel is produced outside of the capillary and then is extruded into the capillary to form a void-free gel-packed capillary. The gel is extruded from a container typically having an inner diameter several orders of magnitude larger than the inner diameter of the capillary into which the gel is extruded. This extrusion process avoids introducing air into the column. However, this process also typically shears the pre-cured gel into irregular chunks on the order of 5–200 μm in length as the gel enters the capillary and packs these chunks together within the capillary to form a void-free packing. Although this process produces many interfaces between the gel clumps, because of the pliant nature of the gel, these interfaces do not noticeably degrade the resolution of chromatographic processes utilizing such gel-packed capillaries. Indeed, even at 50×magnification of the gel-packed capillaries by use of a visible microscope, the interfaces are not visible.

The gel-formation step can be performed by a manufacturer who injects the gel into capillaries that are transferred to the end user or who transfers the gel to an end user for performance of the extrusion step. The entire process disclosed in this application is also applicable to the case in which the manufacturer is also the end user. Before transferring to the end user, the manufacturer can dry the gel to provide it to the user in a more convenient form. This dried gel is referred to herein as a preform. For example, the user can solvate the dried gel with any solvent that is suitable for solvating the dried gel and that is compatible with the user's intended gel chromatography process. Typically, this solvent will be the same as used in the end user's chromatographic process. Transferring the dried gel to the end user reduces the number of end products to be transferred to end users to the number of different dried gels instead of to the number of dried gels times the number of all possible solvents that can be used to solvate these dried gels for use in chromatography. Production of gel preforms for transfer to end users also improves the shelf life of the gel.

The gel can take any convenient form for transfer to the end user, but preferably is in a cylindrical form (a "dried gel worm"). The gel can also be transferred to the end user in a solvated form, but there are several advantages to the user receiving the gel after it has been dried.

The gel can be immersed in a solvent to dissolve out all undesired remnants of the gel formation process, including initiators, catalysts, unreacted monomers, and other low molecular weight species. This step preferably occurs before shipment to the end user. Because of the small diameter of the gel beads and the gel worms, simple immersion of the gel beads and gel worms in a bath of solvent will readily draw these remnants out of the gel. Various absorbants, such as ion exchange resins can be added to the cleansing solvent to aid in the extraction of unwanted residuals. In contrast to this, when the gel formation process takes place in the capillary, only a small fraction of these remnants is removed by immersion of the capillary in a bath of solvent or by passing solvent through the capillary.

This process has a number of advantages over prior methods of producing a gel within a capillary. A major advantage is that it can repeatably produce within the capillary a highly uniform gel that does not electromigrate during electrophoresis and that does not suffer from voids. Such uniformity is important for achieving high resolution in the chromatograph. It is also a much faster process of producing a gel-filled capillary than the moving zone curing process discussed in the Background of the Invention.

The production of the gel outside of the capillary in which the chromatographic separation occurs also introduces a large increase in flexibility in the chemical process of gel formation. For example, the solvent used in initially producing the gel before dehydration can differ from the solvent used during the chromatographic separation of sample components. This greatly increases the flexibility in choice of chemical processes to generate the gel. Also, because the user is not restricted to using the same solvent that was used to generate the gel, the user can solvate the dried gel with any solvent compatible with that gel and with the chromatographic separation process for which the gel will be used. This not only avoids the need of the manufacturer of the gel-filled capillaries to ship as many different products as there are dried-gel/solvent combinations, it also enables the user to utilize the user's own secret solvent. Furthermore, the manufacturer can include a cleaning step to rinse out of the gel unwanted residuals of the gel formation process. This produces a much purer gel that will produce much sharper separation peaks.

Additionally, the gel can be derivatized after it has been polymerized to give it increased selectivity. After the curing step, the worm can be subjected to various reactive chemicals to introduce functionality that would otherwise interfere with the gel polymerization reaction. Such compounds as alkyl groups can be introduced to increase hydrophobicity phenyl groups can be reacted to interact with aromatic species, hydroxyl groups would allow hydrogen bonding during separation. These examples are only illustrative of the possible reactions.

This process makes it possible to mass-produce the gel for extrusion by the end user and avoids the need for the end user to produce the gel. Not only does this save a lot of time for the end user, it also avoids exposing the end user to some of the dangerous chemicals, such as neurotoxins, that are needed to produce some gels. Also, because the gel is produced outside of the end user's environment, more creative solvent chemistry can be utilized in designing the gels.

DESCRIPTION OF THE PREFERRED EMBODIMENT

Figure 4:
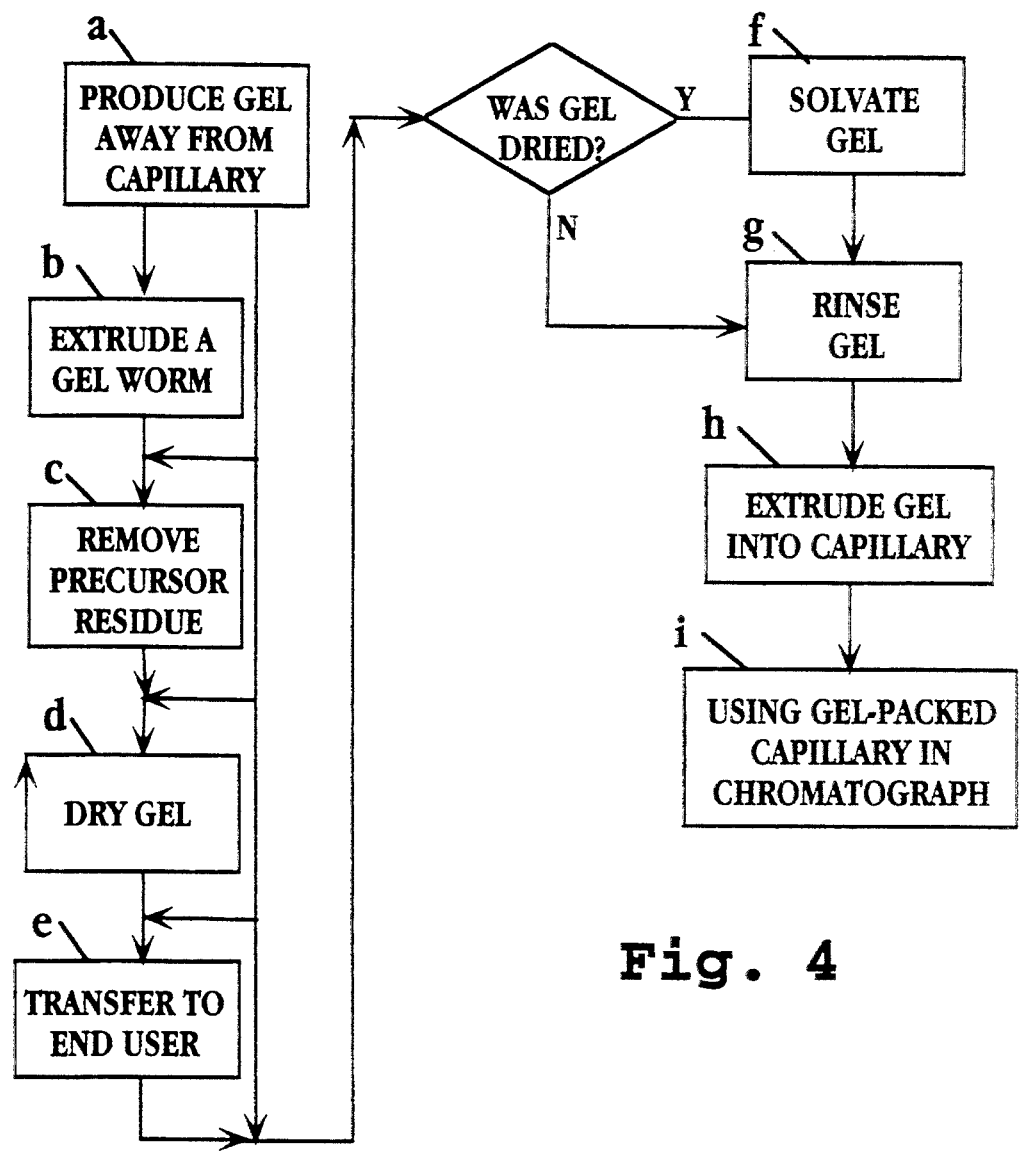
FIG. 4 illustrates the steps of producing a gel outside of a capillary and then extruding the gel into the capillary.

In FIG. 4 is illustrated an improved process for filling a capillary with a gel. In accordance with this process, gel precursor ingredients are mixed in a convenient vessel such as a reaction tube and are enabled to react to form a gel (step 41). Producing the gel in a vessel of convenient laboratory or factory size simplifies the gel formation process compared to producing the gel within a capillary. The various ingredients required for the gel formation process can be easily added to the vessel, stirred to completely mix the ingredients and sampled for quality control.

After the gel has cured, pressure is used to push the gel out of the tube, thereby forming a cylindrical "gel preform". Each preform is then immersed (step 42) for several hours in a solvent selected to dissolve out of that preform various contaminants, including unreacted and partially reacted portions of the gel precursor.

The gel is then air dried, freeze dried or dehydrated in a solvent to the gel (step 43) for several hours to produce a "dried gel preform" that can be transferred to an end user, such as a customer or the manufacturer. Heat, vacuum and/or flowing air can be applied to the gel to enhance the rate of drying.

A solvent for use in a gel chromatograph separation process is selected and a dried preform that is soluble in that solvent. The preform is inserted into a tube 31 and then a fluid is introduced into the tube cavity. A vacuum can be applied to remove any trapped air bubbles. This tube should be sufficiently strong to sustain the pressures needed in a subsequent step of extruding a gel into a capillary. The solvent is poured into this tube to solvate the dried preform (step 44). Tube 31 should have an inside diameter comparable to or slightly smaller than the diameter of the gel worm before it was dried. Preferably, the diameter should be about 85% of the diameter of the gel worm before it was dried because, when the dried gel worm is resolvated, it usually does not expand to its original solvated size. For this choice, when the dried gel is resolvated with an amount of liquid substantially equal to that removed during the drying step 43, the resulting gel will have a pore size substantially equal to that of the original gel worm. If a smaller pore size is desired, then the volume of tube 31 can be less than the volume of the tube in which that gel worm was originally produced.

When the dried gel is solvated, tube 31 is screwed into a coupling, such as dead volume coupling 32, and into a pump 33. It is important that no air is introduced into the gel or between the gel filled tube and the capillary. The pump can be as simple as a syringe or as complicated as a powerful, multipurpose lab pump. Into the other end of coupling 32 is coupled the capillary 15 that is to be filled with the solvated gel. The pump is then activated to extrude the solvated gel into capillary 15. With a pressure on the order of 1,000–10,000 psi, a typical solvated gel can be extruded in about one minute into the entire length of a meter long capillary having an inside diameter of 50–100 $\mu$m. The actual pressure chosen will depend on the modulus of the gel, the diameter of the capillary, the length of the capillary, the breaking strength of the capillary, the availability of a high pressure pump and the amount of time that is acceptable for filling the capillary. However, the pressure should be large enough to drive gel up the tube uniformly within the capillary so that the resolution of the chromatograph process will not be degraded. This gel-filled column is then immediately ready for use. Because the volume of tube 31 is typically a few orders of magnitude greater than the volume of the capillary 15, a comparably large number of capillaries can be filled from a single preform. Because the extrusion process is on the order of a minute, many capillaries can be filled by this process within the time needed to produce a single gel filled capillary by the moving cure zone process discussed above in the Background of the Invention. In addition, the multiple capillaries can be made from one batch of material so that consistency is improved.

Gel-filled capillary 15 is then disconnected and coupled into a gel chromatography apparatus (step 46). Thus, each preform can be utilized in a number of different separation processes equal to the number of useful solvents that can be used to solvate the gel to form a solvated gel that is useful for gel chromatography. Therefore, the availability of gel preforms enables a small number of dried gel worms of varying composition to produce a much larger number of different gels, depending on the choice of solvent used to solvate the dried gel worm.

In the step of solvating the dried preform (step 44), the solvent used in that step need only be compatible with that separation process. The ionic content and concentration can be altered after injection by electrolysis using a solvent containing different ions and/or different ion concentrations.

It is not necessary for all chromatography processes that the gel be rinsed to remove gel precursor residues and other contaminants because such residues and contaminants may not interfere with a particular gel chromatograph process. Therefore, execution of step 42 is optional. Similarly, it is not necessary that the gel be dried before shipment to an end user or use by the gel fabricator. That is, steps 43 and 44 are also optional steps. The various paths in FIG. 4 illustrate that these steps are optional. However, this figure is not intended to be exhaustive in illustrating which of these steps are and are not optional.

The gel can also be used without first being dried if the solvent within the gel at the end of step 41 is compatible with the gel chromatograph process in which the gel is to be used.

It is convenient, but not necessary to use the gel in some form other than solvated or dried gel preform. These alternate gel forms can be exposed to postcure steps such as rinsing to remove unwanted gel formation residues and/or exposure of the cured gel to chemicals that can modify the cured gel, but would interfere with the gel formation process. For example, the gel can be transferred to the end user as dried gel beads and/or as solvated gel beads. In the first of these two cases, the end user solvates the dried gel beads just as is done for the case of a dried gel worm (step 44). The solvated gel beads are then injected into the capillary with sufficient pressure that the beads compress and deform to form a void-free gel-packed column that is packed tightly enough that it does not electromigrate when used in an electrophoretic gel chromatograph process. The beads are injected into the capillary in hydrated form to avoid trapping air in the column and to produce a more uniform gel within the column than would result if the beads were injected in a dried form.

The above process is illustrated by the following examples. Four different gels were formed from the following three stock solutions:

Stock Solution 1: 27 g of acrylamide and 3 g of bis-acrylamide in 73 ml of deionized water;

Stock Solution 2: 0.10M tris-borate, 0.05M sodium chloride and 0.01M EDTA (ethylene diamine tetraacetic acid) in deionized water; and Stock Solution 3: 0.10M tris-glycine, 1.0% sodium dodecyl sulfate in deionized water.

Formulation 1 consists of 1.0 mL of Stock Solution 1 and 1.0 mL of Stock Solution 2 in 8.0 mL of deionized water. Formulation 2 consists of 2.0 mL of Stock Solution 1 and 1.0 mL of Stock Solution 2 in 7.0 mL of deionized water. Formulation 3 consists of 1.5 mL of Stock Solution 1 and 1.0 mL of Stock Solution 3 in 7.5 mL of deionized water. Formulation 4 consists of 2.5 mL of Stock Solution 1 and 2.0 mL of Stock Solution 2 in 5.5 mL of deionized water.

To each formulation is added 0.0075 g of ammonium persulfate and 0.005 mL of tetramethylethylenediamine. Each of these formulations is prepared in a polypropylene beaker and then degassed at 30 mm Hg ambient pressure for five minutes. Each formulation is then poured into a test tube containing a 100 mm by 2 mm stainless steel tube and placed in a nitrogen atmosphere to cure for a minimum of one hour.

Each 2 mm tube of cured gel is then coupled to a fused silica capillary (such as Part #TSP50/350, Part #TSP75/350 or Part #100/350 from PolyMicro Technologies Inc. of Phoenix Arizona) by means of a low dead volume fitting (such as Part #U-437 from Upchurch Scientific Inc. of Seattle Wash.) at one end and onto a high pressure liquid pump (such as the high pressure liquid chromatography pump available on the model 140A from Applied Biosystems, Inc.). The pump is filled with water and used to apply up to 7500 psi to the gel in order to drive it up the capillary. A flow rate of 250 $\mu$L per minute is used and gel is allowed to flow out of the distant end of the capillary for about one minute before the pressure is released.

The gel from three of these formulations was injected into capillaries of diameters 50, 75 and 100 microns inside diameter. The pressure required to push these gels up 20 cm long capillaries of these three inside diameters was: 3,000 psi, 2,200 psi and 1,800 psi, respectively, for Formulation 1; 4,900 psi, 4,200 psi and 1,400 psi, respectively, for Formulation 2; and 5,500 psi, 4,900 psi and 3,300 psi, respectively for Formulation 4.

Figure 1:
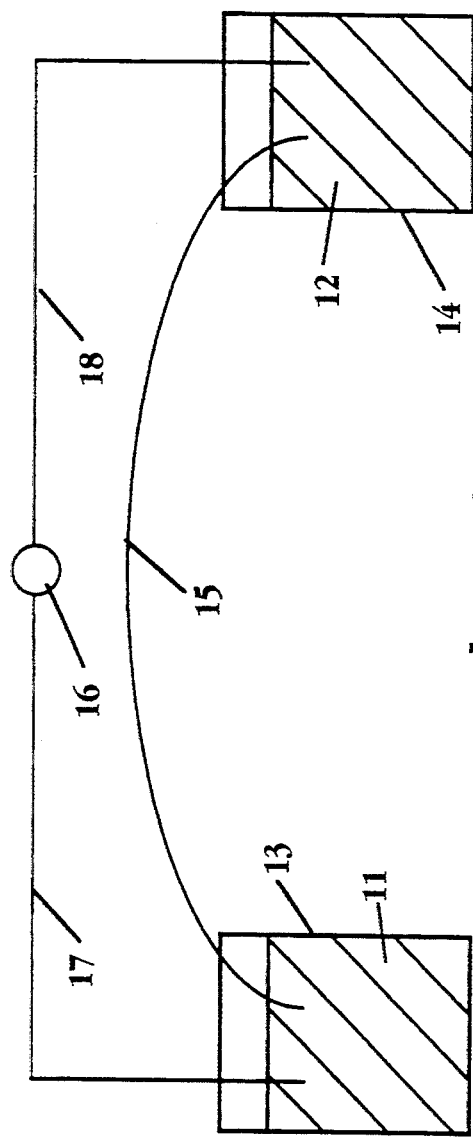
FIG. 1 illustrates an apparatus for electrophoretic separation chromatography.
Figure 2:
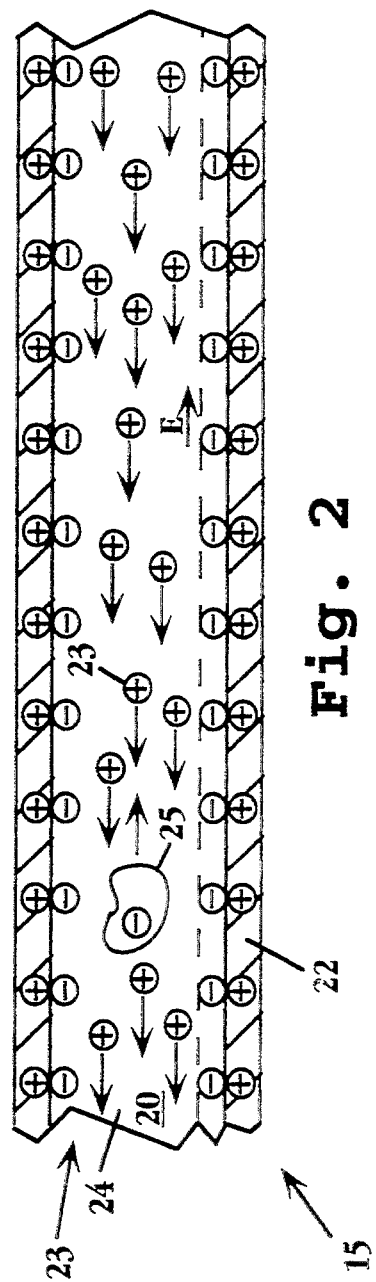
FIG. 2 illustrates in greater detail a small section of capillary 15.
Figure 3:
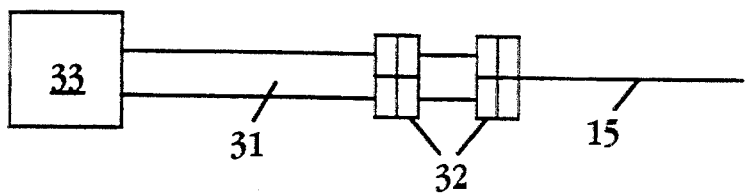
FIG. 3 illustrates an apparatus for extrusion of the gel into the capillary.

The effectiveness of these gel-filled capillaries in electrophoretic separation was then tested on an Applied Biosystems Model 270A Automated Capillary Electrophoresis system for sample solutions containing single stranded DNA, double stranded DNA and proteins. In FIG. 1 is shown an electropherogram for an electrophoretic separation of a one kilobase double stranded DNA ladder through a 45 cm long, 75 $\mu$m capillary filled with Formulation 1 cured gel. The DNA was dissolved in water and electrokinetically injected into the capillary at five kilovolts for five seconds and then the electrophoretic separation was carried out at six kilovolts.

Figure 5:
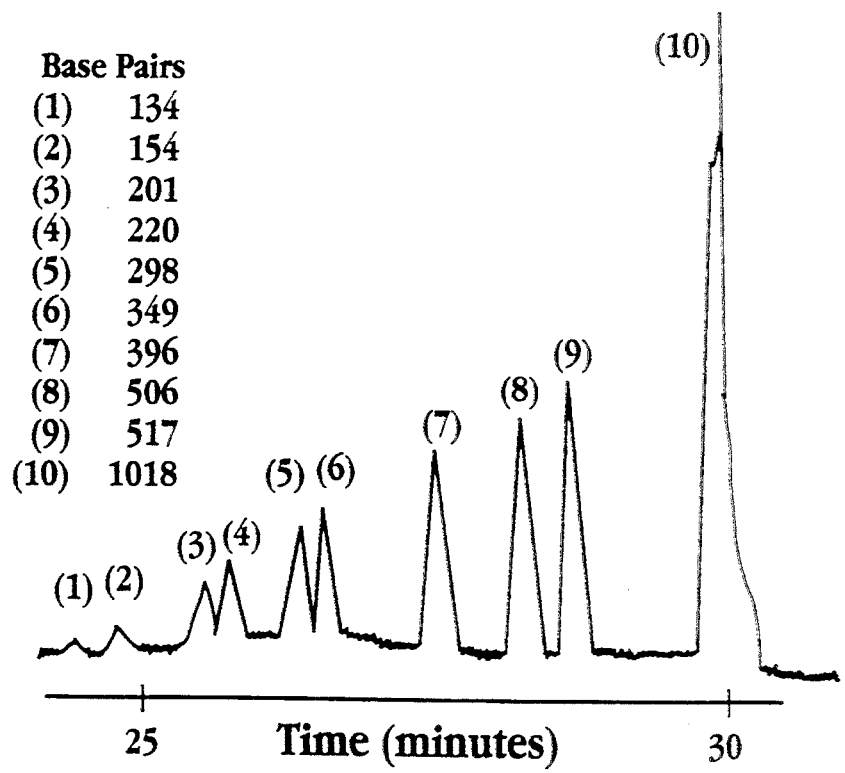
FIGS. 5–7 are electropherograms for separations of DNA and proteins using three different gel-filled capillaries produce in accordance with the process disclosed herein.

In FIG. 5 is shown an electropherogram for an electrophoretic separation of a series of single stranded DNA, polyD(A) with 19 to 24 bases through a 50 cm long, 75 $\mu$m inside diameter capillary filled with Formulation 4 cured gel. The polyD(A) was dissolved in water and electrokinetically injected into the capillary at five kilovolts for two seconds and then the electrophoretic separation was carried out at 20 kilovolts.

Figure 6:
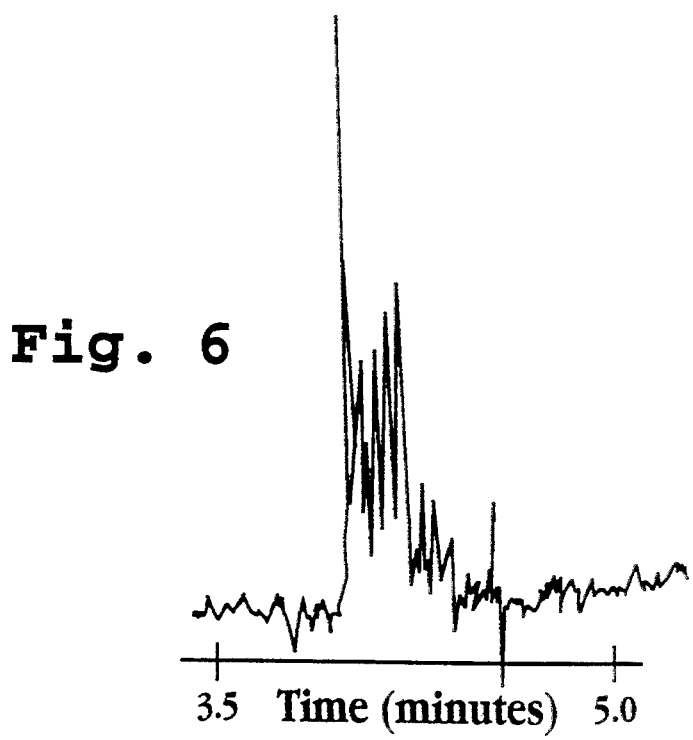
Figure 7:
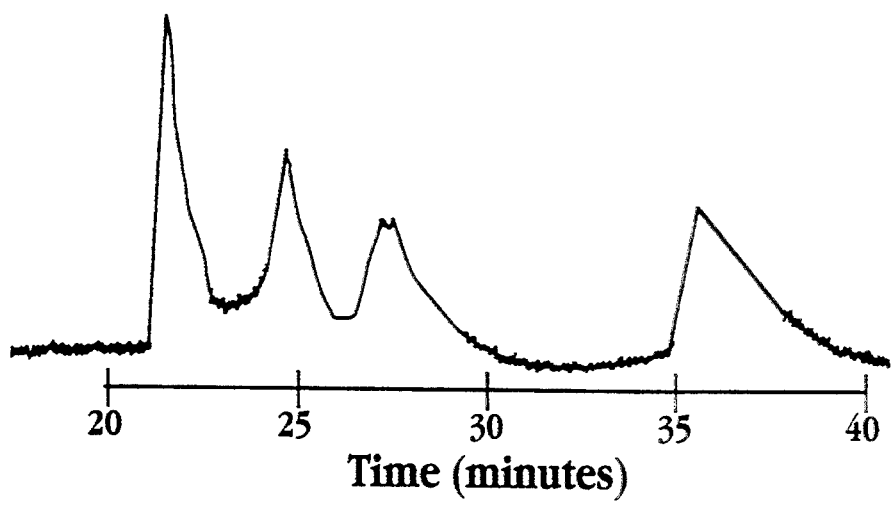

In FIG. 6 is shown an electropherogram for an electrophoretic separation of denatured protein standards through a 50 cm long, 75 $\mu$m inside diameter capillary filled with Formulation 3 cured gel. The protein standards were lactalbumin (molecular weight 14,200), trypsin inhibitor (molecular weight 20,100), trypsinogen (molecular weight 24,000) and carbonic anhydrase (molecular weight 29,000). The proteins were boiled for five minutes in a solution containing one percent mercaptoethanol and sodium dodecyl sulfide. After boiling, this solution was diluted ten to one in a 10 mM tris-glycine solution. The protein mix was electrokinetically injected into the capillary at 5 kilovolts for 15 seconds and then the electrophoretic separation was carried out at 10 kilovolts. These tests show that very good electrophoretic separation is achieved with these gel-filled columns. It is rather surprising that, even though the process of injection of the cured gel into the capillary shreds the cured gel as it is injected into the capillary, the resulting compaction of the gel pieces within the column produces gel-filled column that produces sharp electrophoretic separations of sample solution components.

Gel filled capillaries were also produced using a gel that had been dried and then resolvated before extrusion into a capillary. In one example, the tube containing cured formulation #1 gel was connected at one end to the Applied Biosystems model 140A pump and the other end was left open. The pump was then activated to produce a 250 microliters per minute flow rate to extrude the gel to form a continuous rod. The gel rod was then placed into 500 ml of deionized water for eight hours to remove ammonium persulfate and tetramethylethyleneamine residuals as well as unreacted acrylamide monomer and any noncrosslinked polymer. The gel rod was then transferred into 100 ml of acetone which dehydrated the gel rod. The dehydrated rod was then placed under vacuum for four hours to remove residual acetone.

The dried gel rod was placed into a five centimeter long, 0.040 inch inside diameter stainless steel tube. This tube was then placed into a test tube filled with with 30 mM tris-borate buffer for two hours to hydrate the dried gel rod. This steel tube was then connected to a 50 cm long, 75 $\mu$m inside diameter capillary and the gel was extruded into this capillary in the manner described above.

Figure 9:
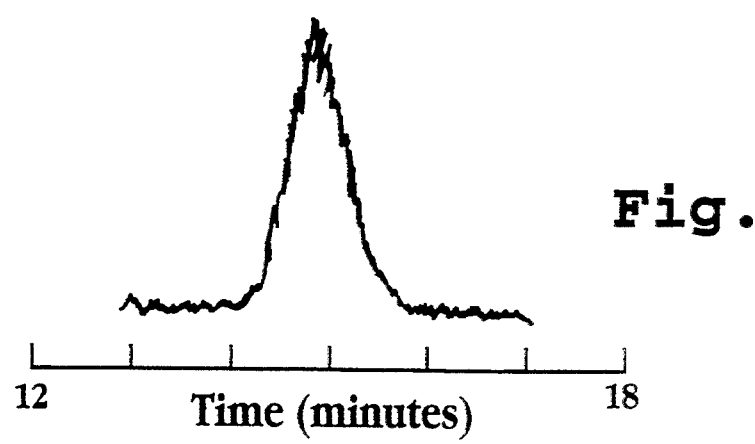
FIG. 9 shows that a capillary filled with gel that has been dried and rehydrated can achieve a single base resolution.

FIG. 9 is an electropherogram utilizing this rehydrated gel to separate polyoligonucliotides, pd(A)4-0-60. The separation was carried out on an Applied Biosystems model 270A automated capillary electrophoresis instrument operated at 15 kilovolts. This figure illustrates that single base separation is achieved with this apparatus.

Figure 8:
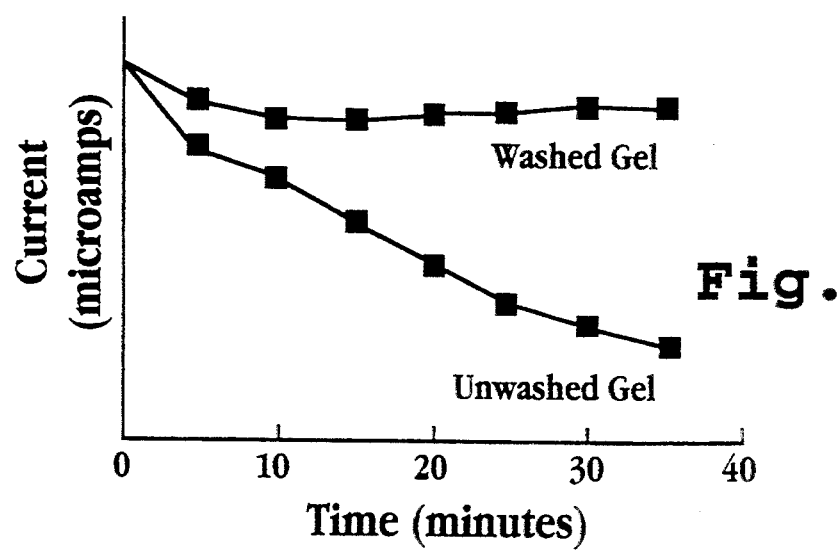
FIG. 8 illustrates that rinsing a gel worm is effective in removing contaminants from the gel worm.

The effectiveness of removing contaminants from the gel by the step of soaking the gel worm in a solvent is illustrated in FIG. 8. In that figure, the current through the capillary is plotted as a function of time for one example in which the gel was not washed and for one example in which the gel was washed. The electrophoretic test run was executed on an Applied Biosystems Model 270A automated capillary electrophoresis instrument operating at 10 kilovolts. The current through the capillary was monitored by a strip chart recorder. FIG. 8 covers a time interval at the beginning of the electrophoretic run. The large drop in current for the unwashed gel compared to the washed gel is symptomatic of impurities being driven from the gel. This shows that the step of washing the gel is effective in removing impurities from the gel.

I claim:

1. A method of forming a void-free gel packed capillary which comprises the steps of:
   (a) forming a cross-linked gel outside of a capillary; and
   (b) forcing the gel into the capillary under conditions which shear the gel into irregular pieces and form a void-free gel with multiple interfaces in the capillary.

2. A method as in claim 1, wherein the gel contains precursor residues and, after step (a) and prior to step (b), removing such residues from the gel.

3. A method as in claim 1, wherein said gel is formed in a solvent, and further comprising between steps (a) and (b) the steps of: drying the gel to remove substantially all solvent from the gel; and resolvating the dried gel.

4. A method as in claim 3, wherein the dried gel is resolvated with a solvent different from that which was removed from the gel by said drying.

* * * * *